United States Patent
Griggs et al.

(10) Patent No.: US 9,609,138 B2
(45) Date of Patent: *Mar. 28, 2017

(54) CROSS-MEDIA VOICE MAIL NOTIFICATION AND DELIVERY

(75) Inventors: Theodore Leon Griggs, Woodside, CA (US); Christopher Michael Waters, Palo Alto, CA (US); Dan Seyer, Palo Alto, CA (US); Peter X. Leong, Los Altos, CA (US)

(73) Assignee: BT Americas Inc., Irving, TX (US)

( * ) Notice: Subject to any disclaimer, the term of this patent is extended or adjusted under 35 U.S.C. 154(b) by 276 days.

This patent is subject to a terminal disclaimer.

(21) Appl. No.: 13/442,338

(22) Filed: Apr. 9, 2012

(65) Prior Publication Data

US 2013/0094632 A1 Apr. 18, 2013

Related U.S. Application Data

(63) Continuation of application No. 11/765,833, filed on Jun. 20, 2007, now Pat. No. 8,155,281.

(51) Int. Cl.
*H04M 1/64* (2006.01)
*H04M 3/533* (2006.01)
*A61K 9/20* (2006.01)
*A61K 31/4025* (2006.01)
*H04L 12/58* (2006.01)
(Continued)

(52) U.S. Cl.
CPC ........... *H04M 3/533* (2013.01); *A61K 9/2054* (2013.01); *A61K 31/4025* (2013.01); *H04L 51/24* (2013.01); *H04M 3/537* (2013.01); *H04M 3/42059* (2013.01); *H04M 3/42102* (2013.01); *H04M 3/53333* (2013.01);
(Continued)

(58) Field of Classification Search
USPC ...................................................... 379/88.22
See application file for complete search history.

(56) References Cited

U.S. PATENT DOCUMENTS

| 5,283,818 A | 2/1994 | Klausner et al. |
| 5,390,236 A | 2/1995 | Klausner et al. |

(Continued)

FOREIGN PATENT DOCUMENTS

| EP | 0876043 A2 | 11/1998 |
| EP | 1599022 A2 | 11/2005 |

(Continued)

OTHER PUBLICATIONS

"U.S. Appl. No. 11/765,833 , Response filed Aug. 3, 2011 to Non Final Office Action mailed Mar. 15, 2011", 12 pgs.

(Continued)

*Primary Examiner* — Joseph T Phan
(74) *Attorney, Agent, or Firm* — Schwegman Lundberg & Woessner, P.A.

(57) ABSTRACT

The subject matter herein relates to voice mail systems and, more particularly, cross-media voice mail notification and delivery. Various embodiments described herein provide systems, methods, software, and data structures that operate to, or facilitate, dispatching of voice mail notification messages to voice mailbox owners. In some embodiments, the notifications are sent to the voice mailbox owners in a text format, such as a short message service text message, email, or other text based service. These and other embodiments are described herein.

13 Claims, 8 Drawing Sheets

(51) Int. Cl.
*H04M 3/537* (2006.01)
*H04M 3/42* (2006.01)

(52) U.S. Cl.
CPC *H04M 2203/152* (2013.01); *H04M 2203/253* (2013.01); *H04M 2203/4536* (2013.01)

(56) References Cited

U.S. PATENT DOCUMENTS

| | | | |
|---|---|---|---|
| 5,450,488 | A | 9/1995 | Pugaczewski et al. |
| 5,524,140 | A | 6/1996 | Klausner et al. |
| 5,572,576 | A | 11/1996 | Klausner et al. |
| 6,233,317 | B1 | 5/2001 | Homan et al. |
| 6,351,764 | B1 * | 2/2002 | Voticky et al. ............ 709/207 |
| 6,411,685 | B1 * | 6/2002 | O'Neal .................. 379/88.14 |
| 6,614,887 | B1 * | 9/2003 | Satapathy et al. ........ 379/88.22 |
| 6,636,733 | B1 | 10/2003 | Helferich |
| 6,671,355 | B1 | 12/2003 | Spielman et al. |
| 6,683,940 | B2 | 1/2004 | Contractor |
| 6,785,379 | B1 | 8/2004 | Rogers et al. |
| 6,891,933 | B2 | 5/2005 | Kumamoto |
| 7,050,792 | B2 * | 5/2006 | Chou et al. ............... 455/412.2 |
| 7,317,788 | B2 | 1/2008 | Caspi et al. |
| 7,317,908 | B1 | 1/2008 | Eason |
| 7,359,493 | B1 * | 4/2008 | Wang et al. ............ 379/88.23 |
| 7,474,741 | B2 | 1/2009 | Brunson et al. |
| 7,480,368 | B2 | 1/2009 | Sipher |
| 7,587,033 | B2 | 9/2009 | Crago et al. |
| 7,636,431 | B2 | 12/2009 | Williams et al. |
| 7,801,286 | B1 * | 9/2010 | Thentheruperai et al. 379/88.25 |
| 8,027,436 | B1 | 9/2011 | Hursey et al. |
| 8,064,367 | B2 * | 11/2011 | Sin et al. .................. 370/259 |
| 8,155,281 | B2 | 4/2012 | Griggs et al. |
| 8,577,967 | B1 * | 11/2013 | Chavez .................. H04L 51/36 709/204 |
| 2003/0228863 | A1 | 12/2003 | Vander Veen et al. |
| 2006/0188084 | A1 | 8/2006 | Rogers et al. |
| 2007/0183407 | A1 | 8/2007 | Bennett et al. |
| 2008/0043939 | A1 | 2/2008 | Sipher |
| 2008/0317222 | A1 | 12/2008 | Griggs et al. |
| 2009/0003540 | A1 | 1/2009 | Zafar |

FOREIGN PATENT DOCUMENTS

| | | |
|---|---|---|
| JP | 10308825 A | 11/1998 |
| JP | 2000020422 A | 1/2000 |
| JP | 2001024798 A | 1/2001 |
| JP | 2001127888 A | 5/2001 |
| JP | 2003348244 A | 12/2003 |
| JP | 2007110769 A | 4/2007 |
| JP | 2008181781 A | 8/2008 |
| JP | 2010530713 A | 9/2010 |
| WO | WO-2004112368 A2 | 12/2004 |
| WO | WO-2008156527 A2 | 12/2008 |
| WO | WO-2008156527 A3 | 9/2009 |

OTHER PUBLICATIONS

"U.S. Appl. No. 11/765,833, Response filed Nov. 17, 2011 to Non Final Office Action mailed Aug. 26, 2011", 10 pgs.

"U.S. Appl. No. 11/765,833, Non Final Office Action mailed Mar. 15, 2011", 9 pgs.

"U.S. Appl. No. 11/765,833, Non Final Office Action mailed Aug. 26, 2011", 6 pgs.

"U.S. Appl. No. 11/765,833, Notice of Allowance mailed Dec. 2, 2011", 8 pgs.

"Australian Application Serial No. 2008267116, Office Action mailed Jun. 29, 2012", 3 pgs.

"Australian Application Serial No. 2008267116, Response filed Oct. 24, 2012 to Office Action mailed Jun. 29, 2012", 22 pgs.

"European Application Serial No. 08767654.0, Office Action mailed Feb. 16, 2012", 5 pgs.

"European Application Serial No. 08767654.0, Office Action mailed Feb. 19, 2013", 6 pgs.

"European Application Serial No. 08767654.0, Response filed Jun. 20, 2012 to Office Action mailed Feb. 16, 2012", 17 pgs.

"International Application Serial No. PCT/US2008/005963, Preliminary Report on Patentability mailed Dec. 21, 2009", 13 pgs.

"International Application Serial No. PCT/US2008/005963, Search Report mailed Aug. 19, 2009", 3 pgs.

"International Application Serial No. PCT/US2008/005963, Written Opinion mailed Aug. 19, 2009", 6 pgs.

"Japanese Application Serial No. 2010-513184, Office Action mailed Nov. 26, 2012", 5 pgs.

"Japanese Application Serial No. 2010-513184, Response filed Feb. 21, 2013 to Office Action mailed Nov. 26, 2012", With English Claims, 13 pgs.

* cited by examiner

FIG. 4

```
YOU HAVE VOICE MAIL MESSAGES

FROM: VOICE MAIL SYSTEM
SUBJECT: YOU HAVE VOICE MAIL MESSAGES

YOU HAVE RECEIVED THE FOLLOWING VOICE MAIL MESSAGES:

[1] 563-556-5105 JOHN SMITH      6/1   13:22
    [2] 212-232-5692 PETER O'MALLY   6/1   13:23
    [3] 651-330-1600 RICH DEERE      5/31  14:01
    [4] 563-583-9944 DONNY OSMUND    5/31  07:30
    [5] 651-549-9697 GUNTHER ROWDY   5/30  09:47

TO DOWNLOAD AND LISTEN TO A MESSAGE, CLICK
HYPERLINKED SENDER NAME.

TO HAVE YOUR TELEPHONE OF RECORD DIALED TO PRESENT
THE MESSAGE TO YOU, CLICK THE HYPERLINKED MESSAGE
NUMBER.

TO LOG INTO YOUR VOICE MAIL ACCOUNT ONLINE, CLICK
HERE.

OTHERWISE, YOU MAY DIAL INTO THE VOICE MAIL SYSTEM BY
CALLING (800) 555-1212.

THANK YOU FOR USING THE VOICE MAIL SERVICE.
```

FIG. 5

| VOICE MAIL FROM JOHN SMITH |
|---|

FROM: VOICE MAIL SYSTEM
SUBJECT: VOICE MAIL FROM JOHN SMITH

JOHN SMITH HAS LEFT YOU A 23 SECOND MESSAGE.

TO DOWNLOAD AND LISTEN TO THIS MESSAGE, CLICK HERE.

TO HAVE YOUR TELEPHONE OF RECORD DIALED TO PRESENT THE MESSAGE TO YOU, CLICK HERE.

TO LOG INTO YOUR VOICE MAIL ACCOUNT ONLINE, CLICK HERE.

OTHERWISE, YOU MAY DIAL INTO THE VOICE MAIL SYSTEM BY CALLING (800) 555-1212.

THANK YOU FOR USING THE VOICE MAIL SERVICE.

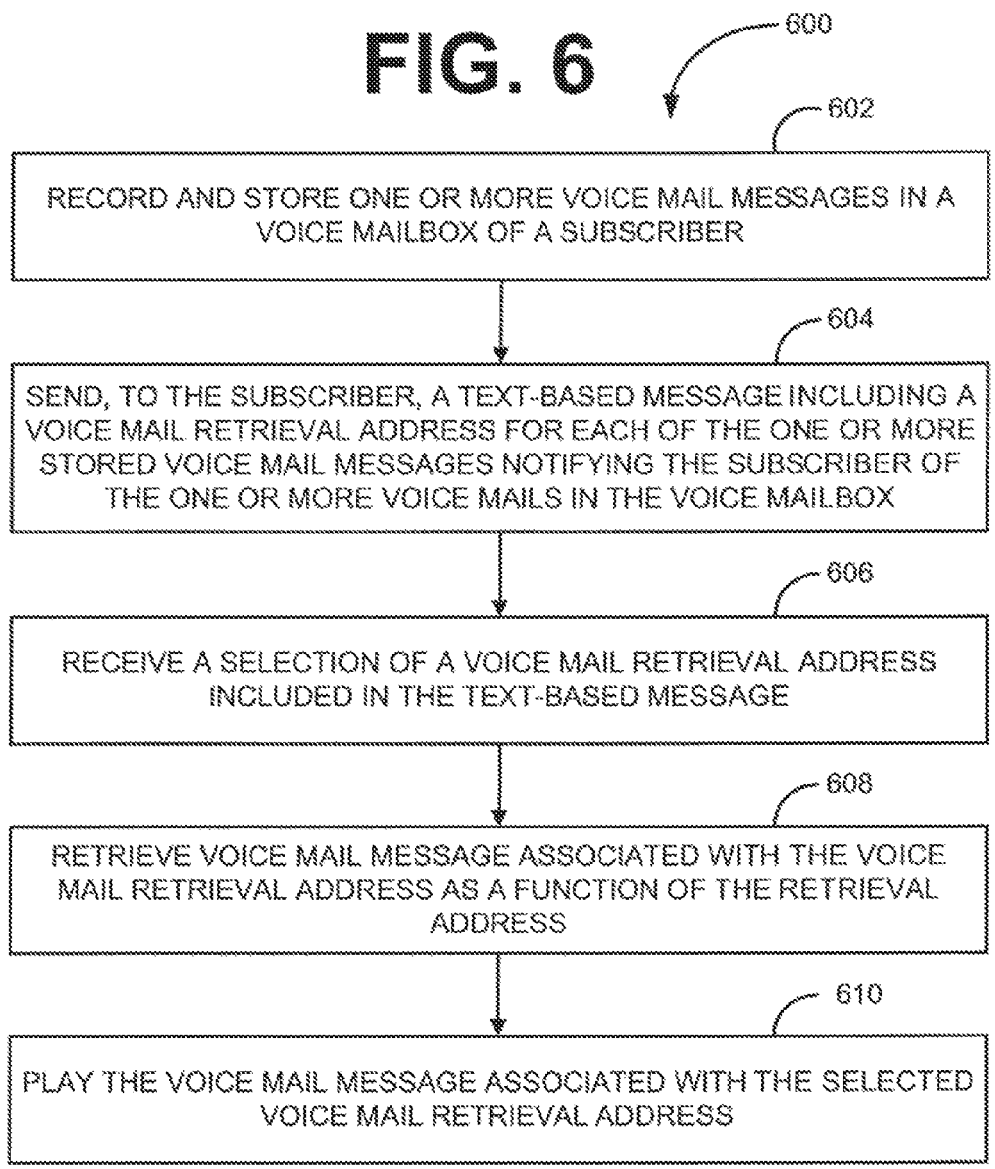

FIG. 7

| MAILBOX | |
|---|---|
| MAILBOX_ID | NAME |
| 0001 | JOHN SMITH |
| 0002 | GARY WILEY |
| 0003 | MARTHA ANDERSON |
| 0004 | JOEY JOHNSON |
| . | . |
| . | . |
| . | . |

| MESSAGES | |
|---|---|
| MESSAGE_ID | MESSAGE |
| 0001 | 000001121.WAV |
| 0002 | 000001122.WAV |
| 0003 | 000001123.WAV |
| 0004 | 000001124.WAV |
| . | . |
| . | . |
| . | . |

| MAILBOX_PHONE_NO | | |
|---|---|---|
| MAILBOX_ID | PHONE_NO | TYPE |
| 0001 | 5635551212 | LL |
| 0001 | 5635551213 | WL |
| 0002 | 5635555152 | VOIP |
| 0003 | 6126362565 | VOIP |
| 0004 | 6195854751 | LL |
| 0004 | 6192726464 | WL |
| 0004 | 6195486521 | VOIP |
| . | . | |
| . | . | |
| . | . | |

| VM_BOX | | | | |
|---|---|---|---|---|
| MAILBOX_ID | CALLER | MESSAGE_ID | LENGTH | RET_ADD |
| 0001 | 5635555152 | 0001 | 1:23 | 6085125555 |
| 0001 | 5635555152 | 0002 | 0:22 | 6085125556 |
| 0004 | 5635551213 | 0003 | 0:15 | 6085125555 |
| . | . | | | |
| . | . | | | |
| . | . | | | |

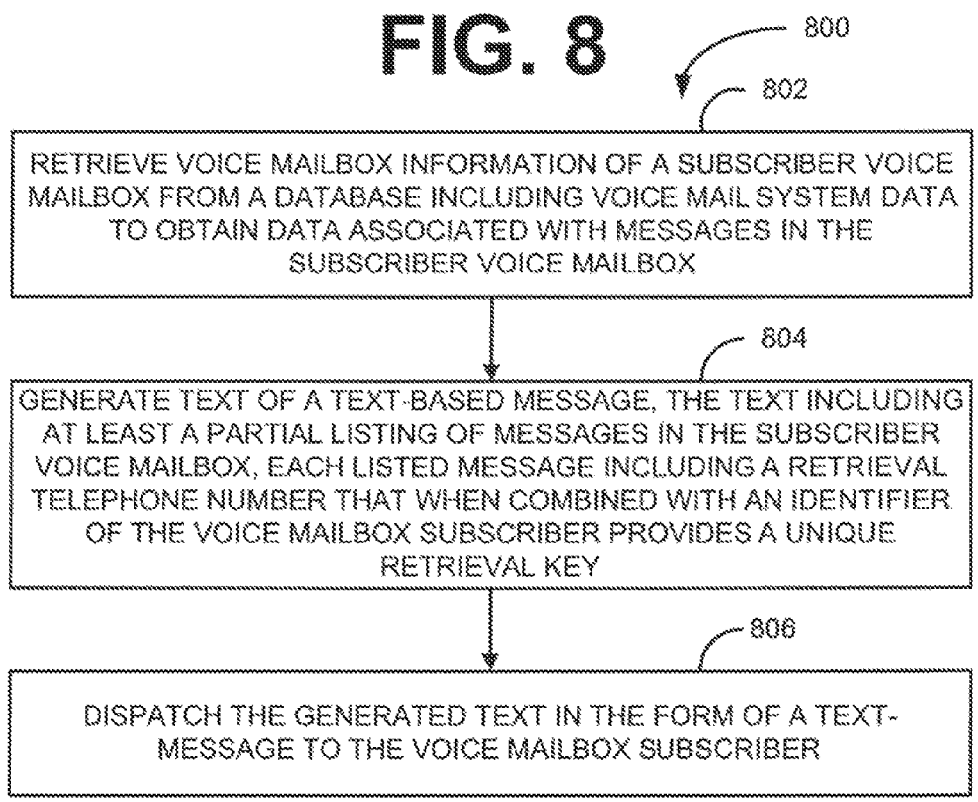

CROSS-MEDIA VOICE MAIL NOTIFICATION AND DELIVERY

CLAIM OF PRIORITY

This application is a continuation of and claims the benefit of priority under 35 U.S.C. §120 to U.S. patent application Ser. No. 11/765,833, filed on Jun. 20, 2007, which is hereby incorporated by reference herein in its entirety.

TECHNICAL FIELD

The subject matter herein relates to voice mail systems and, more particularly, cross-media voice mail notification and delivery.

BACKGROUND INFORMATION

Voice mail systems have generally remained in the same audio-only form for over the last twenty years. A landline telephone may illuminate a light or a mobile telephone may illuminate a symbol indicating a voice mail has been left for the telephone, however, the number of messages is unknown. Further, the senders of these messages are unknown until each voice message is retrieved individually.

Further, when listening to voice mail, the messages are presented in only a single manner, first-in-first-out. Thus, if a more important message is received most recently, all preceding messages must first be listened to even if they are not deemed important.

BRIEF DESCRIPTION OF THE DRAWINGS

FIG. 4 is an email user interface diagram according to an example embodiment.

FIG. 5 is an email user interface diagram according to an example embodiment.

FIG. 6 is a block flow diagram of a method according to an example embodiment.

FIG. 7 is a database diagram according to an example embodiment.

FIG. 8 is a block flow diagram of a method according to an example embodiment.

DETAILED DESCRIPTION

Figure 1:
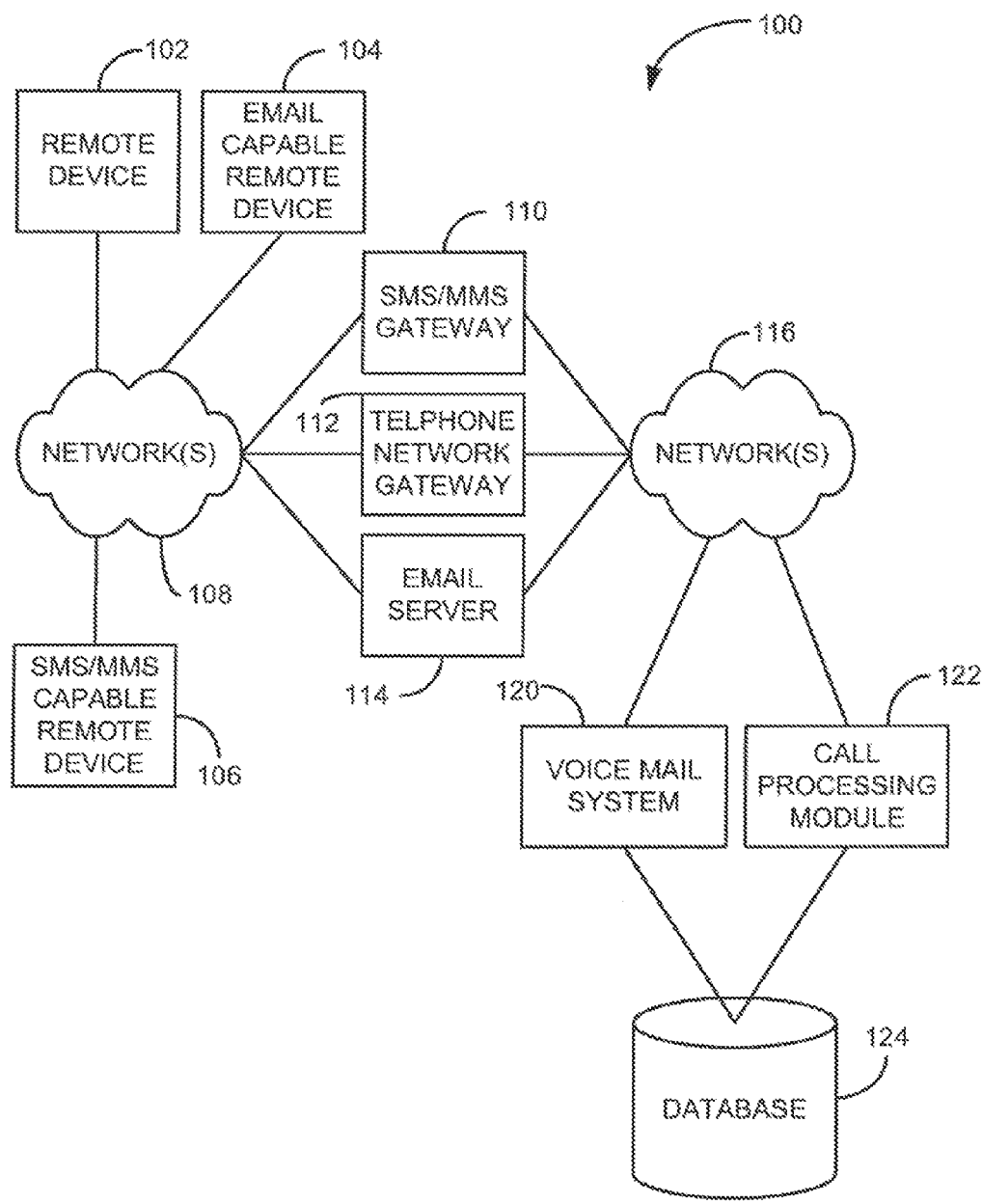
FIG. 1 is a logical block diagram of a system according to an example embodiment.

Two of the most used services that cell phones provide are voice mail and short-message service ("SMS"). While the short message service evolved to the multimedia message service and provided for access to rich content, the voice mail services on cell-phones have typically been isolated, standalone, and have had an interface that has generally remained in the same audio-only form over the last 20 years.

One of the biggest drawbacks of not only cell-phone voice mail, but also most voice mail systems in general, is the lack of information about the contents of a phone's voice mailbox. Typically, the only information conveyed to the end-user is the message-waiting indicator, which only shows whether there are unheard messages in the voice mailbox.

The user, once the knows he has messages, must call into the voice mail system to retrieve his messages. If there are multiple messages, the user must listen to each message in sequence. If there is one particular message that the user wants to hear, having to skip through intervening messages is a nuisance.

Various embodiments described below provide systems, methods, software, and data structures to utilize a mobile phone's existing SMS/MMS capability to enhance the voice mail interface, such that a user can view information about each voice mail and then retrieve a specific voice mail from a list without having to listen to the other messages in the voice mailbox. Some of these embodiments, and others, may also or alternatively use email to convey information about waiting voice mails and facilitate retrieval of a specific voice mail message without having to listen to the other waiting messages.

In the following detailed description, reference is made to the accompanying drawings that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed.

The following description is, therefore, not to be taken in a limited sense, and the scope of the inventive subject matter is defined by the appended claims.

The functions or algorithms described herein are implemented in hardware, software or a combination of software and hardware in one embodiment. The software comprises computer executable instructions stored on computer readable media such as memory or other type of storage devices. Further, described functions may correspond to modules, which may be software, hardware, firmware, or any combination thereof. Multiple functions are performed in one or more modules as desired, and the embodiments described are merely examples. The software is executed on a digital signal processor, ASIC, microprocessor, or other type of processor operating on a system, such as a personal computer, server, a router, or other device capable of processing data including network interconnection devices.

Some embodiments implement the functions in two or more specific interconnected hardware modules or devices with related control and data signals communicated between and through the modules, or as portions of an application-specific integrated circuit. Thus, the exemplary process flow is applicable to software, firmware, and hardware implementations.

FIG. 1 is a logical block diagram of a system 100 according to an example embodiment. The example system 100 may include several remote devices such as remote device 102, an email capable remote device 104, a short message service ("SMS") or multimedia message service ("MMS") remote device 106, or other remote device such as a personal computer. Some remote devices may also include one or more of landline, wireless, or Voice Over Internet Protocol ("VoIP") telephone capabilities.

Each of the remote devices includes a connection to one or more networks 108. The one or more networks 108 may include one or more of a public switched telephone network, a wireless telephone network, a shared global computing network such as the Internet, a local area network, a wide area network, and other network types capable of transporting voice and/or data signals.

The example system 100 also includes gateways that facilitate communication of data and voice signals to and from a voice mail system 120. The gateways may include an SMS/MMS gateway 110, a telephone network gateway 112, and an email server 114. The gateways are connected to the voice mail system via one or more networks 116. The one or more networks 116 may include one or more of the same networks as the one or more networks 108. However, in some embodiments, the networks 116 include a local area network that interconnects the gateways with the voice mail system 120 and a call processing module 122.

The voice mail system 120 includes hardware and software to terminate calls, play prompts, get input from callers, and record and store voice messages. The voice mail system 120 may also include a set of addresses that may be used by a telephone network of the networks 108 and 116 to route telephone calls to the voice mail system.

The call processing module 122 includes the application level logic that drives interactions with calls and callers. The call processing module 122 in some embodiments include text to voice engines, voice recognition objects, and other services to facilitate caller interaction with the voice mail system. The call processing module 122 may access data in the voice mail system 120 and data stored in a database 124 to determine how to process and route calls.

The database 124 further includes data to assist the voice mail system in processing voice mail messages. The database 120 also typically includes a voice mail message record for each voice mail left for a subscriber of the voice mail system 120. A voice mail message record typically includes header data of a message and a pointer to a location where a corresponding voice mail message recording is stored. In some embodiments, the header data of a voice mail message includes data from a call that yielded the voice mail message. This data may include caller identification data of the caller, such as the telephone number called from, a name of the caller or registered name of an account holder of the telephone number called from, and a date and time of the call. The header data may also include a duration of a recorded message, an indicator of message urgency input by the caller leaving the message, and a name selected from a directory of the voice mailbox subscriber as a function of the phone number called. This may result in two names in a header record. However, in some embodiments, a single name is in the header record that is selected based on a policy set by an administrator of the voice mail system 120 or the voice mailbox subscriber.

In one example scenario, a caller may call a voice mail system 120 subscriber's remote device, which in this scenario is a mobile telephone. When the mobile telephone rings a configured number of times, such as four, the subscriber's mobile phone carrier, when the subscriber's mobile phone account with the carrier is properly configured, will route the call to the voice mail system 120 over the telephone network gateway 112. In some embodiments, the voice mail system 120 is a voice mail system 120 maintained by the carrier. In other embodiments, the voice mail system 120 is a separate voice mail system 120 of a voice mail service provider.

When the telephone call is routed to the voice mail system 120 the call processing module 122 provides prompts to the caller to leave a message. The voice mail system 120 and call processing module 122 store information about the caller, such as a number called from and a name of the caller or holder of the telephone number called from. This information, reined to as message header data, plus the duration of a message left and the message are also stored. In some embodiments, this information is stored in the database 124. The recorded message may be stored in the database 124 or in a separate location. If stored in a separate location, or a database 124 table other than the table within which the message header data is stored, a pointer is included with the message header data that may be used to retrieve the recorded voice message.

After a voice message is left for a subscriber, the subscriber may be notified of the message. In some embodiments, the subscriber is notified periodically of messages received, such as hourly, daily, or some other periodic basis as configured by the subscriber, a voice mail system 120 administrator, default policy of the voice mail system 120, or other setting.

The voice mailbox subscriber may be notified, in various embodiments, via an SMS or MMS text message to the mobile telephone called by one or more callers leaving messages in the voice mail system for the subscriber. In these and other embodiments, the subscriber may also be notified via email.

When a condition specified by one or more configuration settings specifies when to notify the subscriber of messages is met, the voice mail system will retrieve the header information of received messages and generate a notification for dispatch to the subscriber. The voice mail system 120 determines how the notification is to be sent and formats the notification message appropriately. The voice mail system 120 also retrieves an address of the subscriber to which the notification is to be sent. The address may be a mobile telephone number, an email address, or other address to which a notification may be configured to be sent.

Once the notification is properly formatted and addressed, the voice mail system 120 sends the message with address to the proper gateway. This may include the SMS/MMS gateway 110, the email server 114, or other gateway depending on the particular embodiment and configuration of the subscriber voice mailbox. In some embodiments, the notification may be sent to more than one address of the subscriber or other address held by someone other than the subscriber depending on the configuration of the subscriber's voice mailbox. For example, a subscriber may choose to have the notification also or alternatively sent to a spouse, a secretary, or other.

In some embodiments, the voice mail system 120 may also be configured to send a notification message immediately upon receipt of a message marked by a caller as urgent. In other embodiments, a configuration of a voice mailbox may be made to specify that if a subscriber has not accessed the voice mail system 120 at least once aver a certain period, such as twenty-four hours, a notification message will be sent to another address. This may be useful in situations where a voice mailbox subscriber is on vacation such a scenario, the notification may be sent to the subscriber's secretary, business partner, or personal mobile telephone to help ensure messages do not go unchecked.

In some embodiments, a subscriber may send a text message from a mobile telephone, or other remote device, or an email, to the voice mail system to request a listing of voice messages in the subscriber voice mailbox. In such instances, the voice mail system 120 will reply to the request with the notification message.

Example notification messages are illustrated in FIG. 2, FIG. 3, FIG. 4, and FIG. 5.

In some embodiments, a subscriber may have more than one phone number associated with a single voice mailbox. In such instances, each phone number is configured to forward calls to the voice mail system 120 after a certain number of rings.

When a subscriber receives a voice mail notification message, the subscriber is presented with the ability to call into the voice mail system 120 to retrieve a specific message regardless of the order in which the voice messages were received or in which the voice mail system 120 may typically present voice mail messages. In such embodiments, when a notification of new message is sent to a subscriber, each voice mail included in the notification includes an address with which that message can be retrieved directly. In some embodiments, the address is a retrieval telephone number and, in the case of an SMS/MMS capable remote device 106, selection of the address will cause the device 106 to dial the retrieval telephone number. The voice mail system 120 indexes and associates the retrieval telephone phone numbers, subscriber's telephone number, and unique messages. Thus, when a subscriber calls a particular retrieval telephone number associated with a particular message from a device that presents as the automatic number identification ("ANI") of the calling party one of the one or more numbers for which the subscriber configured voice mail service, the voice mail system 120, using the combination of retrieval telephone number and subscriber's ANI as the message index, retrieves the target message. The number called from (ANI), and the number called (retrieval telephone number), operate together to form a unique index to any single message. Thus, the retrieval telephone numbers of the voice mail system can be used for multiple subscribers because the retrieval telephone number itself is only half of the message index. The other half of the message index, the subscriber's telephone number, is unique to the subscriber.

There may be virtually any number of retrieval telephone numbers. However, the more retrieval telephone numbers, the more messages subscribers may retrieve directly. One thousand numbers are used in one embodiment, while other embodiments include ten, 100, and 200.

When a subscriber deletes a message associated with a retrieval telephone number, that number is again available for association with a new message for that subscriber. When one subscriber deletes a message associated with a retrieval telephone number, there is no affect on the association of that retrieval telephone number for any other subscriber for which the retrieval telephone number and subscriber's telephone number form an index to that other subscriber. If the retrieval telephone numbers are exhausted for a particular subscriber, any number of algorithms may be used to reclaim numbers for reuse for that subscriber. The algorithms may include calculations to reclaim the retrieval telephone numbers associated with the oldest messages in the subscriber's voice mailbox. In other embodiments, algorithms may automatically delete voice messages after a certain number of days, reducing the likelihood of running out of numbers. In other embodiments, a subscriber may select or create a rule or rules used by the reclamation algorithms to reclaim retrieval telephone numbers based on calling party information (e.g. unlisted numbers, unknown callers, or specific NPA-NXX-LINE patterns), association with address-book tags (e.g. 'business', 'personal', etc.), address book field contents (e.g. e-mail address or website domain), subscriber-compiled preferred caller lists (e.g. calls from specific work or family members), or other rules.

Figure 2:
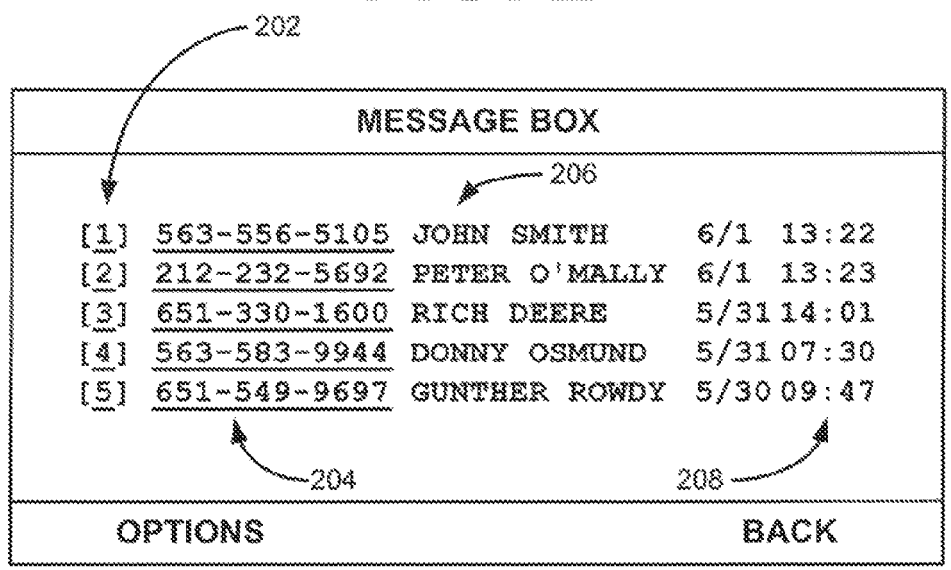
FIG. 2 is a text message user interface diagram according to an example embodiment.

FIG. 2 is a text message user interface diagram according to an example embodiment. The illustrated text message user interface is a text message inbox, such as on a modern mobile telephone or other device capable of receiving a text message. Although a text message inbox is discussed in the context of a mobile telephone, other embodiments may include an instant messaging application, such as Blackberry Messenger available on telephones available from Research in Motion of Waterloo, Ontario, Canada or other instant messaging applications that are operable on any number of personal computers, handheld devices, and other platforms such as Yahoo instant Messenger, AOL, Skype, Google Talk, etc.

The text message user interface diagram presents a message number 202 that may be selected within the user interface to retrieve a specific message on the mobile telephone. Note that the numbers underlined 1-5 indicate that selection of these numbers will cause the mobile telephone to dial a telephone number or trigger another device to retrieve the specific message.

The text message user interface diagram also includes a telephone number 204, if available from caller ID information received with the call, from which each message was received. Each message may also include a name of the caller 206 that left the associated message, if available from caller ID information received with the call, or from a directory stored in the voice mail system by the subscriber. A date and time 208 that each message was received is also presented. Some embodiments may also include other information in the notification message such as a duration of each message. In some embodiments, where the user interface illustrates multiple notification messages received, a subscriber may select one of these messages from the text message inbox view of FIG. 2 to view further message details included in a notification message and be provided with further options.

Figure 3:
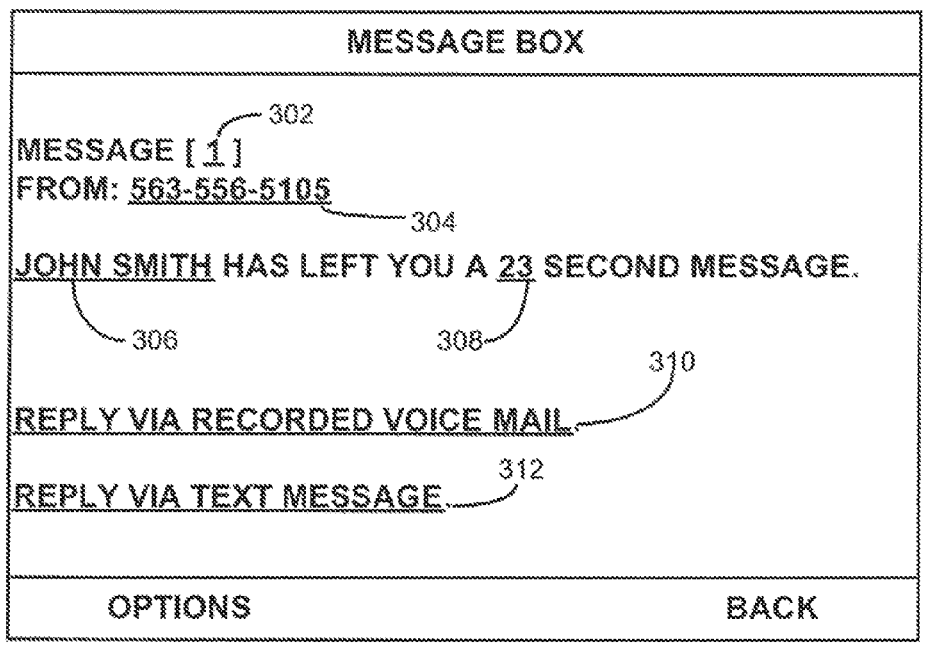
FIG. 3 is a text message user interface diagram according to an example embodiment.

FIG. 3 is a text message user interface diagram according to an example embodiment. This text message user interface diagram includes a more detailed notification message. This message may include a more verbose description of the message. However, the message still includes a selectable message number 302 which will cause the mobile telephone to dial into the voice mail system to retrieve the specific message. The name of the caller 306 is also provided, if available, along with an indicator of message duration 308.

The notification message may also include an option to reply to the caller with a recorded message. The user may select "Reply via recorded voice mail" 310. In such a scenario, the selection of this option causes the subscriber's mobile telephone to call into the voice mail system and allows the subscriber to record a message. The voice mail system knows who the subscriber is and what action to take, in some embodiments, as a function of a number called and the number called from. These two numbers are used by the voice mail system in such embodiments as an index to determine what action to take.

The subscriber is then prompted by the voice mail system to record a message. Once finished, the voice mail system will send the voice mail message to the caller's voice mail account if the caller is also a subscriber to the voice mail system, or set up an ad hoc account. If an ad hoc account is setup, the caller will be notified of the message via an SMS or MMS message to the caller's mobile telephone. However, if the caller did not call from a mobile telephone, some embodiments may still allow recording of a message if the caller is included in a directory of the called subscriber that includes either a mobile telephone number or an email address. Thus, the voice mail system may alternatively lookup a mobile telephone number or email address of the caller to provide the reply via recorded voice mail functionality.

Similarly, a subscriber may choose the option to "Reply Via Text Message" 312. If the caller calls from a mobile telephone, selection of this option allows the subscriber to send a text message to that device. Alternatively, as above, if a mobile phone number or email address exists in a directory of the subscriber, the user may still reply via text. The text message, once entered by the subscriber will be sent to the voice mail system and then forwarded to the mobile telephone, or converted to an email and sent as an email.

FIG. 4 and FIG. 5 are email user interface diagrams according to example embodiments. The email user interfaces include hyperlinks which may be selected to allow a subscriber to directly retrieve a specific message from the voice mil system. In some embodiments, the hyperlinks will invoke a VoIP service on a computing device within which the email user interface diagram is displayed. In such instances, the VoIP service will either automatically dial or allow the user to dial a specified phone number to retrieve a particular message.

FIG. 6 is a block flow diagram of a method 600 according to an example embodiment. The example method 600 is a method of operation of a voice mail system. In some embodiments, the method 600 includes recording and storing one or more voice mail messages in a voice mailbox of a subscriber 602 and sending, to the subscriber, a text-based message including a voice mail retrieval address for each of the one or more stored voice mail messages notifying the subscriber of the one or more voice mails in the voice mailbox 604. The method 600 may further include receiving a selection of a voice mail retrieval address included in the text-based message 606. After receiving the selection of the voice mail retrieval address, the method 600 includes retrieving the voice mail message associated with the voice mail retrieval address as a function of the retrieval address 608 and playing it 610.

In some embodiments, storing a voice mail message includes storing the message associated with a telephone number of the subscriber for whom the voice mail was left and further associating that message with a voice mail retrieval address. The voice mail retrieval address in association with one or more of the subscriber's telephone numbers forms a unique index to the stored message.

FIG. 7 is a database diagram according to an example embodiment. The database diagram includes tables with columns and rows that may exist in a relational database management system. The tables include MAILBOX, MAILBOX_PHONE_NO, VM_BOX, and MESSAGES.

The MAILBOX table, as illustrated, includes the columns MAILBOX_ID, and NAME. The table may include more columns, but this is sufficient for this simple example. Each row of the MAILBOX table is a voice mail account in a voice mail system. In embodiments where a single phone number is associated with a voice mail account, a phone number column may also be present. However, in the present example embodiment, multiple phone numbers may be associated with a voice mail account using the MAILBOX_PHONE_NO table.

The MAILBOX_PHONE_NO includes columns MAILBOX_ID, PHONE_NO, and TYPE. The MAILBOX_ID column is a foreign key to the same column in the MAILBOX table allowing rows of the MAILBOX_PHONE_NO table to be joined to rows of the MAILBOX table. More than one row may exist for each MAILBOX_ID. Each row includes a phone number in the PHONE_NO column and a type of device for the phone number in the TYPE column. The various types include landline, wireless, VoIP, and other telephone types depending on the embodiment. Thus, a voice mail account in this embodiment may be associated with more than one phone number. In other embodiments, the subscriber's communication device may be addressed with a uniform resource identifier ("URI") in which case the PHONE_NO for the MAILBOX_ID will be a URI for that subscriber's device.

The VM_BOX table holds header data of received voicemail messages. The columns of the VM_BOX table include MAILBOX_ID, CALLER, MESSAGE_ID, LENGTH, RET_ADD, and other columns depending on the embodiment. These columns may also differ between embodiments depending on the requirements, computing environment, and configuration of the particular embodiment. A VM_BOX record exists for each voice mail message recorded by a voice mail system. The MAILBOX_ID column is a foreign key to the same column in the MAILBOX table allowing rows of the MAILBOX_PHONE_NO table to be joined to rows of the MAILBOX table. Voice mail messages may be retrieved for a particular MAILBOX row corresponding to a voice mail subscriber account as a function of a MAILBOX_ID. The CALLER column holds a phone number of a caller leaving a voice mail message. The MESSAGE_ID column is a foreign key column that allows joining of a VM_BOX record to a record in a MESSAGES table that also includes a MESSAGE column holding a recorded voice mail message. Returning to the VM_BOX table, the LENGTH column holds a time value of a length of the corresponding message stored in the MESSAGES table. The RET_ADD column holds a retrieval address that can be a phone number or other address, such as a universal resource indicator ("URI"), which may be used by a subscriber to retrieve the message corresponding to the VM_BOX record.

In some embodiments, a subscriber may wish to retrieve a specific message stored in the database of FIG. 7 after receiving a voice mail notification message, such as a text message including a listing of waiting voice mails each including a retrieval address. The retrieval address may be a phone number. When the subscriber calls the phone number, such as RET_ADD of the first record in the VM_BOX table. The subscriber calls the phone number 608-512-5555 from phone number 563-555-1212. The voice mail system in such an instance will know that the caller is attempting to retrieve a specific message based on the number called. The voice mail system will then use the called-from phone number to retrieve a MAILBOX_ID from the MAILBOX_PHONE_NO table. The voice mail system will retrieve a MAILBOX_ID of 0001 as a function of the called-from phone number 563-555-1212. Then the voice mail system has a MAILBOX_ID of 0001 and a called phone number of 608-512-5555 which are used to retrieve a MESSAGE_ID of 0001. At this point, the desired message is identified. The voice mail system then retrieves and plays message 000001121.WAV from the MESSAGE table using MESSAGE_ID 0001.

Note that a retrieval address may be concurrently used for a multitude of separate voice mail subscriber accounts. In some embodiments, the only constraint is that each phone number associated with a voice mail account only be associated with a single voice mail account. Alternatively, stated otherwise, each phone number in the PHONE_NO column of the MAILBOX_PHONE_NO table must be unique.

FIG. 8 is a block flow diagram of a method 800 according to an example embodiment. The example method 800, and the other methods described herein, may be encoded as instructions on a tangible computer-readable medium to cause a computing system to perform the method. The instructions may execute on one computer or multiple computers.

In some embodiments, the example method 800 includes retrieving voice mailbox information of a subscriber voice mailbox from a database including voice mail system data to obtain data associated with messages in the subscriber voice mailbox 802. The method 800 also includes generating text of a text-based message, the text including at least a partial listing of messages in the subscriber voice mailbox, each listed message including a retrieval telephone number that when combined with an identifier of the voice mailbox subscriber provides a unique retrieval key 804. After the text is generated 804, the method 800 includes dispatching the generated text in the form of a text-message to the voice mailbox subscriber 806.

In some embodiments, the method 800 also includes receiving a telephone call to a retrieval telephone number from a telephone number associated with the subscriber and retrieving a voice mail message as a function of the retrieval telephone number and the telephone number associated with the subscriber. Such embodiments further include playing the voice mail message.

It is emphasized that the Abstract is provided to comply with 37 CFR, §1.72(b) requiring an Abstract that will allow the reader to quickly ascertain the nature and gist of the technical disclosure. It is submitted with the understanding that it will not be used to interpret or limit the scope or meaning of the claims.

In the foregoing Detailed Description, various features are grouped together in a single embodiment to streamline the disclosure. This method of disclosure is not to be interpreted as reflecting an intention that the claimed embodiments of the inventive subject matter require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. A communication system, comprising:
a voice mail system having one or more processors, the voice mail system being configured to couple to one or more telephone networks to receive telephone calls, the received telephone calls being to leave messages or to retrieve messages, the voice mail system further to
record and store one or more voice mail messages in a voice mailbox of a subscriber,
send, to the subscriber, a text-based message including, for each of the one or more stored voice mail messages:
a voice mail retrieval address to retrieve the specific voice mail message,
a link to send a reply text message to a sender of the specific voice mail message, and
a link to send a voice mail reply to a received voice mail.

2. The communication system of claim 1, wherein the voice mail system is further to:
generate a text-based message including information about the one or more recorded voice mail messages in the subscriber voice mailbox and the retrieval address for each of the one or more recorded voice mail messages; and
dispatch the generated text-based message to the voice mailbox subscriber.

3. The communication system of claim 1, further comprising:
a telephone network connection module to communicatively couple to the one or more telephone networks and to provide a telephone number of a caller and a telephone number called; and
a telephone call processing module to process telephone calls received from the one or more telephone networks and to route the telephone calls to the voice mail system.

4. The communication system of claim 3, wherein the voice mail system is further to:
receive a telephone call routed from the telephone network connection module to the voice mail system by the telephone call processing module;
retrieve a voice mail message as a function of a telephone number of the caller and a telephone number called; and
play the voice mail message to the caller.

5. The communication system of claim 4, wherein the telephone number called is the retrieval address of the recorded voice mail message.

6. The communication system of claim 1, wherein at least one of the one or more telephone networks are configured to transport text-based messages including short message service ("SMS") messages.

7. The communication system of claim 1, further comprising a text messaging gateway to couple to at least one of the one or more networks to transport text-based messages.

8. The communication system of claim 1, further comprising a database to manipulate data including the voice mail message header data and provide pointers to the stored recorded voice mail messages.

9. A method comprising:
recording and storing one or more voice mail message in a voice mailbox of a subscriber;
sending, to the subscriber, a text-based message including, for each of the one or more stored voice mail messages:
a voice mail retrieval address to retrieve the specific voice mail message,
a link to send a reply text message to a sender of the specific voice mail message, and
a link to send a voice mail reply to a received voice mail.

10. The method of claim 9, further comprising:
receiving a selection of a link to send a reply text message to a sender of a voice mail message and text for the reply text message; and
forwarding the received text for the text message as a text message to the sender of the voice mail.

11. The method of claim 9, further comprising:
receiving a selection of a link to send a voice mail reply to a receive voice mail;
initiating a phone call on a telephone from which the selection was received and prompting a caller to record the voice mail reply;
recording and storing the voice mail reply; and
sending a notification to the sender of the voice mail that a voice mail reply is waiting.

12. The method of claim 11, wherein the notification of the waiting voice mail reply is sent via text message to a phone number from which the voice mail sender left the voice mail.

13. The method of claim 11, wherein the voice mail reply is stored in an ad hoc account if the voice mail sender is not a voice mail system subscriber and the notification text message includes instructions to retrieve the voice mail reply.

* * * * *

UNITED STATES PATENT AND TRADEMARK OFFICE
CERTIFICATE OF CORRECTION

| | |
|---|---|
| PATENT NO. | : 9,609,138 B2 |
| APPLICATION NO. | : 13/442338 |
| DATED | : March 28, 2017 |
| INVENTOR(S) | : Griggs et al. |

Page 1 of 1

It is certified that error appears in the above-identified patent and that said Letters Patent is hereby corrected as shown below:

In Column 3, Line 31, delete "120" and insert --124-- therefor

In Column 4, Line 2, delete "reined" and insert --referred-- therefor

In Column 4, Line 53, delete "aver" and insert --over-- therefor

In Column 4, Line 56, delete "vacation" and insert --vacation. In-- therefor

In Column 7, Line 17, delete "mil" and insert --mail-- therefor

Signed and Sealed this
Tenth Day of July, 2018

Andrei Iancu
*Director of the United States Patent and Trademark Office*